US00PP30894P2

(12) United States Plant Patent
Head et al.

(10) Patent No.: US PP30,894 P2
(45) Date of Patent: Sep. 24, 2019

(54) ***GARDENIA* PLANT NAMED 'RLH-GA1'**

(50) Latin Name: *Gardenia augusta*
Varietal Denomination: RLH-GA1

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select, Inc., Seneca, SC (US)

( * ) Notice: Subject to any disclaimer, the term of this patent is extended or adjusted under 35 U.S.C. 154(b) by 0 days.

(21) Appl. No.: 15/999,866

(22) Filed: Aug. 23, 2018

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Gardenia* plant named 'RLH-GA1', characterized by its compact, upright to outwardly spreading and mounding plant habit; moderately vigorous growth habit; freely branching habit with short internodes; dense and bushy appearance; plants require minimal pruning; flexible lateral branches that resist cracking and splitting; relatively small and dark green-colored leaves; color is maintained during the winter and under low and high light conditions; freely flowering habit with flowering continuous during the spring and early summer; strongly fragrant single white-colored flowers that become yellow in color with development; and excellent garden performance and temperature tolerance.

4 Drawing Sheets

Botanical designation: *Gardenia augusta.*
Cultivar denomination: 'RLH-GA1'.

BACKGROUND OF THE INVENTION

The present invention relates to a new and distinct cultivar of *Gardenia* plant, botanically known as *Gardenia augusta* and hereinafter referred to by the name 'RLH-GA1'.

The new *Gardenia* plant is a naturally-occurring branch mutation of *Gardenia augusta* 'Daisy', not patented. The new *Gardenia* plant was discovered and selected by the Inventor as a single flowering plant from within a population of plants of 'Daisy' in a controlled environment in Seneca, S.C. in 2010.

Asexual reproduction of the new *Gardenia* plant by semi-hardwood and hardwood stem cuttings in a controlled greenhouse environment in Seneca, S.C. since 2011 has shown that the unique features of this new *Gardenia* plant are stable and reproduced true to type in successive generations.

SUMMARY OF THE INVENTION

Plants of the new *Gardenia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'RLH-GA1'. These characteristics in combination distinguish 'RLH-GA1' as a new and distinct *Gardenia* plant:

1. Compact, upright to outwardly spreading and mounding plant habit.
2. Moderately vigorous growth habit.
3. Freely branching habit with short internodes; dense and bushy appearance; plants require minimal pruning.
4. Flexible lateral branches that resist cracking and splitting.
5. Relatively small and dark green-colored leaves; color is maintained during the winter and under low and high light conditions.
6. Freely flowering habit with flowering continuous during the spring and early summer.
7. Strongly fragrant single white-colored flowers that become yellow in color with development.
8. Excellent garden performance and temperature tolerance.

Plants of the new *Gardenia* can be compared to plants of the mutation parent, 'Daisy'. Plants of the new *Gardenia* differ primarily from plants of 'Daisy' in the following characteristics:

1. Plants of the new *Gardenia* are more compact than plants of 'Daisy'.
2. Plants of the new *Gardenia* are more outwardly spreading than and not as upright as plants of 'Daisy'.
3. Plants of the new *Gardenia* have a slower growth rate than plants of 'Daisy'.
4. Plants of the new *Gardenia* are more freely branching than plants of 'Daisy'.
5. Plants of the new *Gardenia* have slightly smaller flowers than plants of 'Daisy'.

Plants of the new *Gardenia* can also be compared to plants of *Gardenia jasminoides* 'Radicans', not patented. In side-by-side comparisons, plants of the new *Gardenia* and 'Radicans' differ primarily in the following characteristics:

1. Plants of the new *Gardenia* are more mounding than and not as outwardly creeping as plants of 'Radicans'.
2. Plants of the new *Gardenia* have a slower growth rate than plants of 'Radicans'.
3. The plant habit of the new *Gardenia* is denser and bushier than and not as open as the plant habit of 'Radicans'.
4. Plants of the new *Gardenia* are more freely flowering than plants of 'Radicans'.
5. Plants of the new *Gardenia* produce single-type flowers whereas plants of 'Radicans' produce double-type flowers.
6. Plants of the new *Gardenia* are more low temperature tolerant than plants of 'Radicans'.
7. Plants of the new *Gardenia* are more freely flowering than plants of 'Radicans'.

BRIEF DESCRIPTION OF THE PHOTOGRAPHS

The accompanying colored photographs illustrate the overall appearance of the new *Gardenia* plant showing the colors as true as it is reasonably possible to obtain in colored reproductions of this type. Colors in the photographs may differ slightly from the color values cited in the detailed botanical description which accurately describe the colors of the new *Gardenia* plant.

The photograph on the first sheet comprises a side perspective view of a typical flowering plant of 'RLH-GA1' grown in an outdoor nursery.

The photograph on the second sheet is a close-up view of a typical plant of 'RLH-GA1' with developing flower buds, developing flowers and fully opened flowers.

The photograph on the third sheet is a close-up view of a typical plant of 'RLH-GA1' with developing flowers and fully opened flowers.

The photograph on the fourth sheet is a close-up view of a typical plant of 'RLH-GA1' with developing flower buds, fully opened flowers and flowers that have turned yellow in color with subsequent development.

DETAILED BOTANICAL DESCRIPTION

The aforementioned photographs and following observations, measurements and values describe plants grown during the spring and early summer in seven-gallon containers in outdoor nurseries in El Campo and Fort Worth, Tex. and under cultural practices typical of commercial *Gardenia* production. During the production of the plants, day temperatures averaged 24° C. and night temperatures averaged 14° C. Plants were three years old when the photographs and the description were taken. In the following description, color references are made to The Royal Horticultural Society Colour Chart, Fifth Edition, except where general terms of ordinary dictionary significance are used.

Botanical classification: *Gardenia augusta* 'RLH GA1'.

Parentage: Naturally-occurring branch mutation of *Gardenia augusta* 'Daisy', not patented.

Propagation:

*Type*.—By semi-hardwood and hardwood stem cuttings.

*Time to initiate roots, summer*.—About 10 to 14 days at temperatures about 27° C. to 30° C.

*Time to initiate roots, winter*.—About 18 to 25 days at temperatures about 16° C. to 17° C.

*Time to produce a rooted young plant, summer*.—About 45 to 60 days at temperatures about 27° C. to 30° C.

*Time to produce a rooted young plant, winter*.—About 60 to 80 days at temperatures about 16° C. to 17° C.

*Root description*.—Fine to medium in thickness, fibrous; white, close to 155A in color.

*Rooting habit*.—Freely branching; dense.

Plant description:

*Plant and growth habit*.—Compact, upright to outwardly spreading and mounding plant habit; moderately vigorous growth habit; relatively slow growth rate; freely branching habit with short internodes; dense and bushy appearance; plants require minimal pruning; freely flowering habit with numerous single-type flowers developing continuously during the spring and early summer.

*Plant height*.—About 52 cm.

*Plant diameter*.—About 61 cm.

Lateral branch description:

*Length*.—About 25 cm to 33 cm.

*Diameter*.—About 7 mm.

*Internode length*.—About 1 cm.

*Strength*.—Strong; lateral branches are flexible and resist cracking and splitting.

*Aspect*.—Upright to outwardly spreading.

*Texture and luster, developing*.—Smooth, glabrous; matte.

*Texture and luster, mature*.—Woody, glabrous; matte.

*Color, developing*.—Close to 146A tinged with close to 166B.

*Color, mature*.—Close to 166A with waxy cuticle, close to 191D.

Leaf description:

*Arrangement*.—Opposite, simple.

*Leaf retention*.—Very good leaf retention has been observed on plants of the new *Gardenia* during the winter.

*Length*.—About 4 cm to 4.5 cm.

*Width*.—About 2 cm to 2.5 cm.

*Shape*.—Elliptic to oblanceolate.

*Apex*.—Acute.

*Base*.—Cuneate to attenuate.

*Margin*.—Entire.

*Venation pattern*.—Pinnate.

*Texture and luster, upper surface*.—Pubescent; coriaceous, tough; glossy.

*Texture and luster, lower surface*.—Pubescent; coriaceous, tough; matte.

*Color*.—Developing leaves, upper surface: Close to 137A. Developing leaves, lower surface: Close to 146B to 146C. Fully expanded leaves, upper surface: Darker green than N137A; venation, close to 146A to 146B; color is retained during the winter and under full sun or shade conditions. Fully expanded leaves, lower surface: Close to 146B to 146C; venation, close to 146C.

*Petioles*.—Length: About 4 mm. Diameter: About 2 mm. Texture and luster, upper and lower surfaces: Smooth, glabrous; slightly glossy. Color, upper surface: Close to 146A to 146B. Color, lower surface: Close to 146B to 146C.

Flower description:

*Flower arrangement and habit*.—Single rotate flowers facing mostly upright and developing in pairs at terminals and sub-terminals; single whorl of five petals fused towards the base into a slender tapering tube; freely flowering habit with numerous flowers developing continuously during the spring and early summer.

*Fragrance*.—Strongly fragrant; sweet and pleasant.

*Natural flowering season*.—Plants of the new *Gardenia* flower continuously during the spring and early summer in Texas.

*Flower longevity*.—Individual flowers last about one to two days on the plant, dependent on ambient temperatures and water status; flowers not persistent.

*Flower diameter*.—About 5.25 cm.

*Flower length* (*depth*).—About 4 cm.

*Flower buds*.—Length: About 3.4 cm. Diameter: Distally, about 6 mm and proximally, about 3 mm. Shape: Roughly ovoid with long tube. Color: Distally, close to 144A and proximally, close to 144B to 144C.

*Petals*.—Quantity and arrangement: About six in a single whorl. Lobe length: About 2.5 cm. Lobe width: About 1.7 cm. Tube length: About 3 mm. Tube diameter: Distally, about 4.5 mm and proximally, about 3 mm. Lobe shape: Broadly ovate to roughly spatulate. Lobe apex: Rounded acute. Lobe margin: Entire, slightly undulate. Texture and luster, upper surface: Smooth, glabrous; velvety; somewhat glossy. Texture and luster, lower surface: Smooth, glabrous; velvety; matte. Color: When opening, upper and lower surfaces: Close to NN155A to NN155B. Fully opened, upper and lower surfaces: Close to NN155A to NN155B; with development, color becoming yellow, close to 160A and eventually, close to 12A.

*Sepals*.—Arrangement: Star-shaped calyx with six sepals fused at the base. Length: About 1.6 cm. Width: About 2.5 mm. Shape: Lanceolate. Apex: Sharply acute. Margin: Entire. Texture and luster, upper and lower surfaces: Smooth, glabrous; slightly glossy. Color, upper surface: Close to 144A. Color, lower surface: Close to 144A to 144B.

*Peduncles*.—Length: About 4 mm. Diameter: About 2 mm. Angle: Upright. Strength: Strong, flexible. Texture and luster: Smooth, glabrous; slightly glossy. Color: Close to 144A to 144B.

*Reproductive organs*.—Stamens: Quantity: Six per flower. Anther size: About 1.2 cm by 1.5 mm. Anther shape: Lanceolate. Anther color: Close to 163A to 163B. Pollen amount: Moderate. Pollen color: Close to 12A. Pistils: Pistil length: About 3.6 cm. Style length: About 2.5 cm. Style color: Close to NN155A to NN155B. Stigma size: About 1.1 cm by 5 mm. Stigma shape: Bulbous. Stigma color: Close to between 7A to 9A. Ovary color: Close to 160A.

*Seeds and fruits*.—To date, seed and fruit development have not been observed on plants of the new *Gardenia*.

Garden performance: Plants of the new *Gardenia* have been observed to have good garden performance and to tolerate wind and temperatures ranging from about −22° C. to about 45° C.

Pathogen & pest resistance: To date, plants of the new *Gardenia* have not been observed to be resistant to pests and pathogens common to *Gardenia* plants.

It is claimed:

1. A new and distinct *Gardenia* plant named 'RLH-GA1' as illustrated and described.

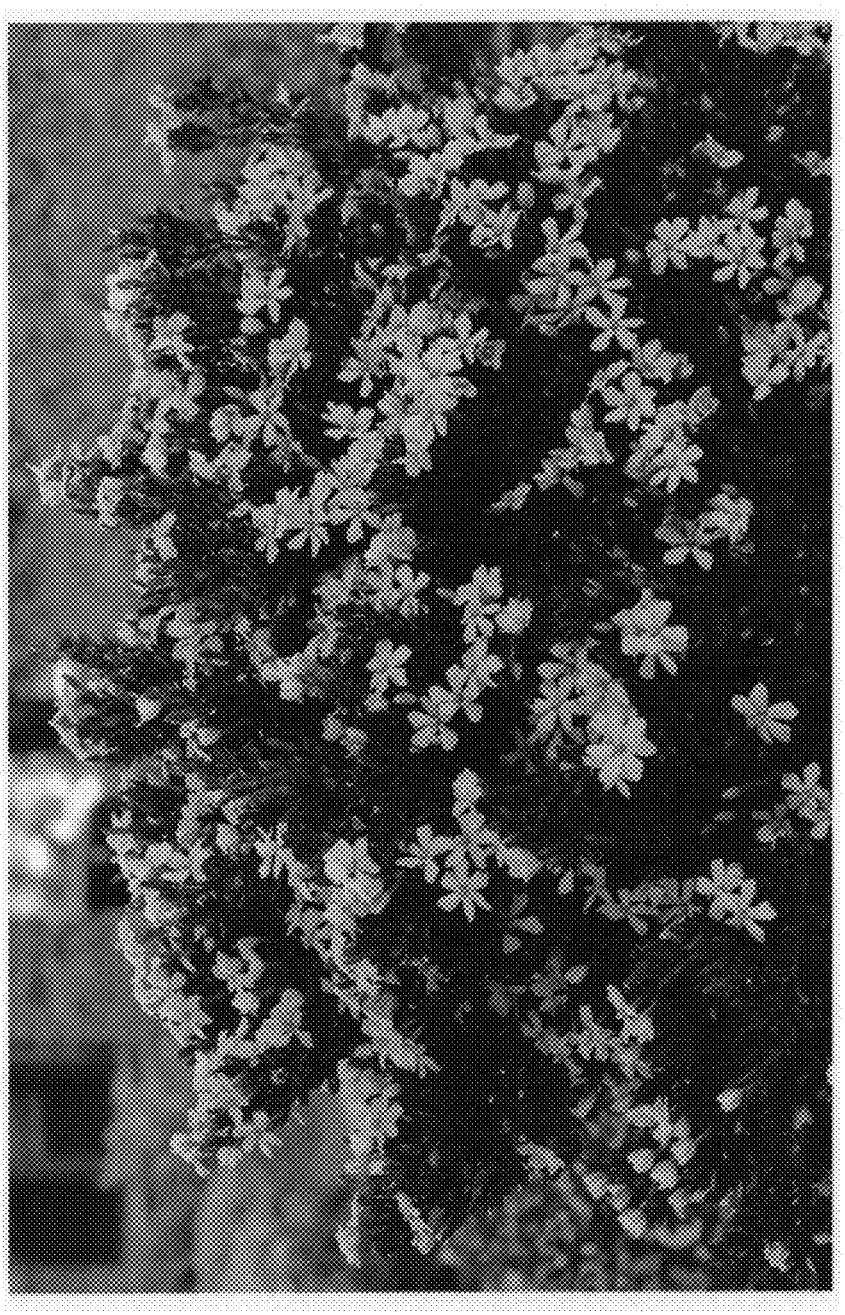

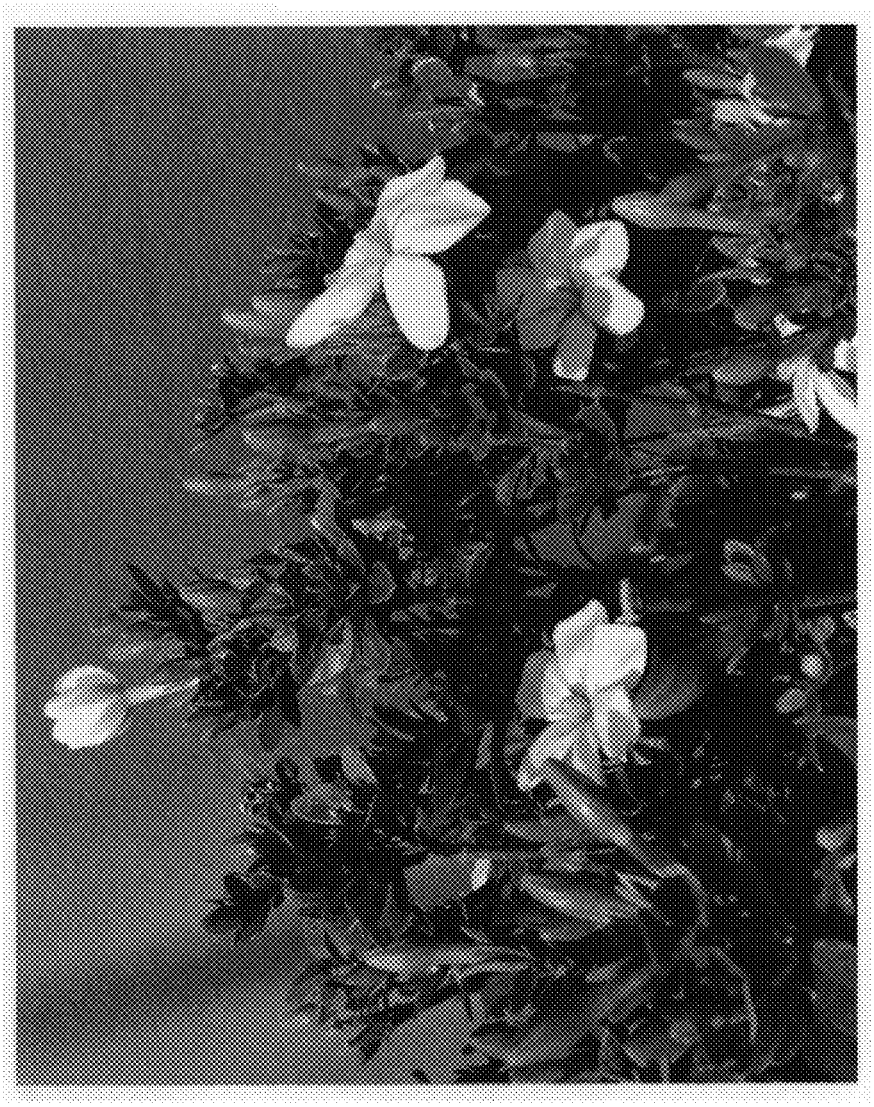

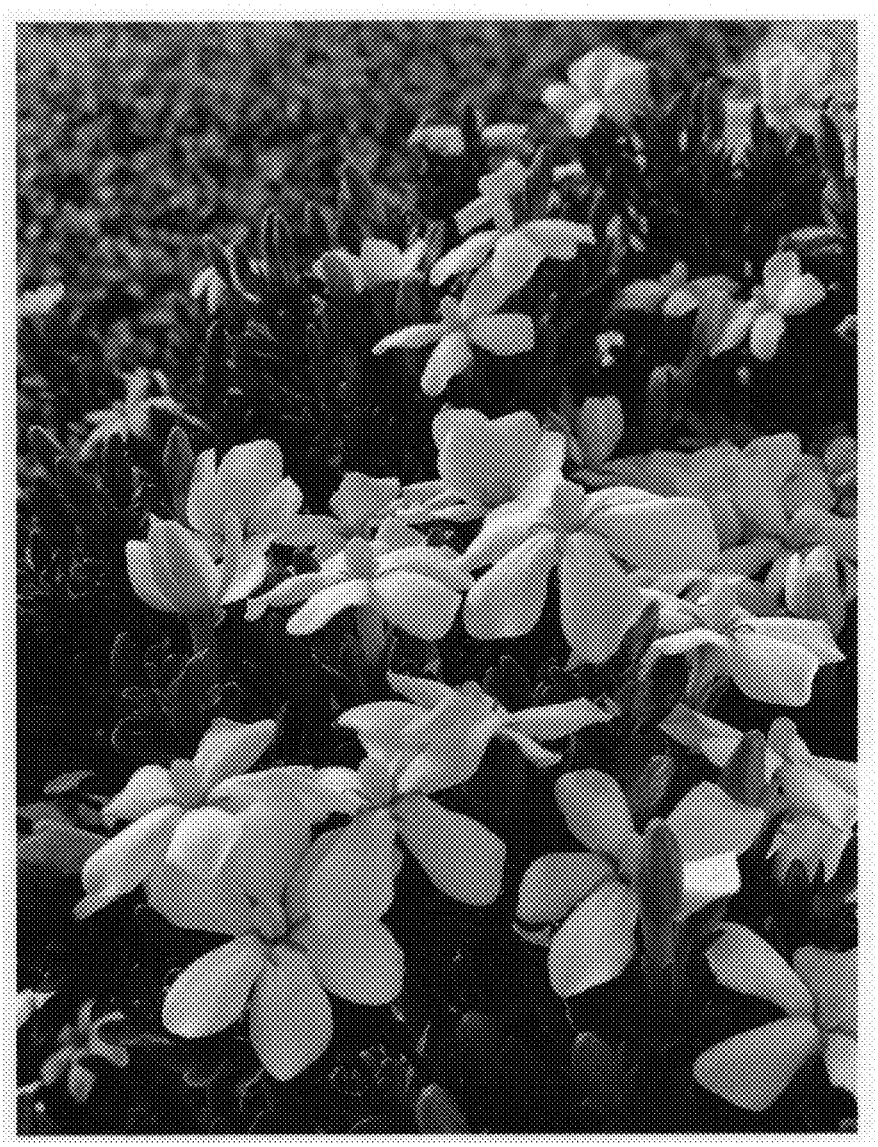

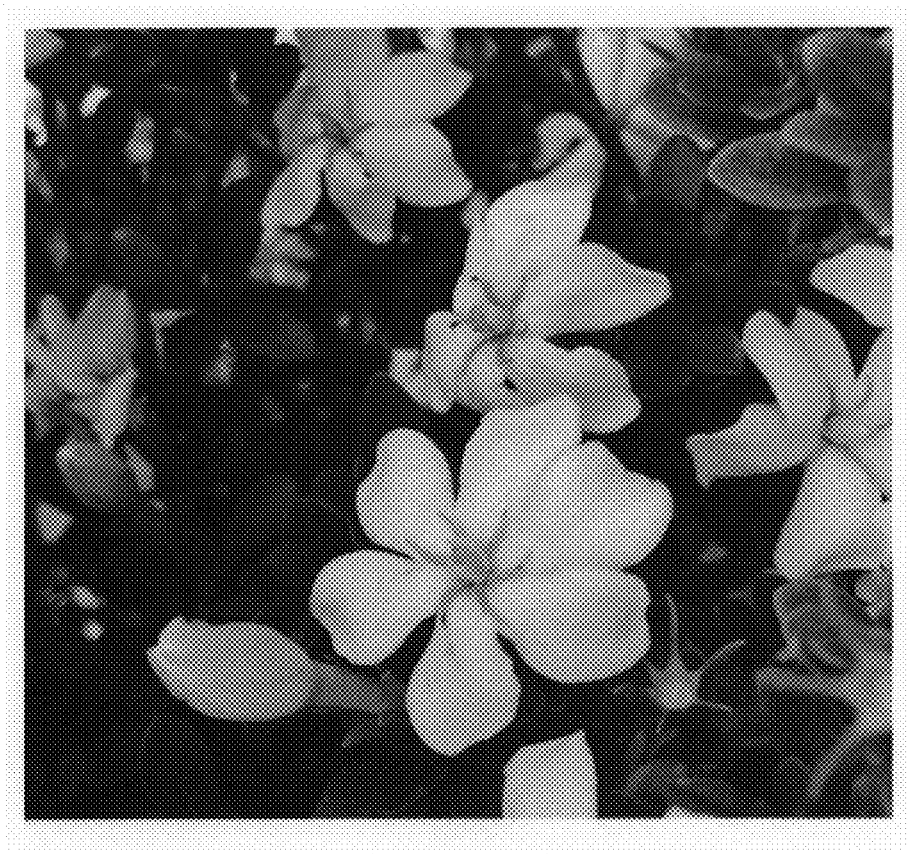

* * * * *